United States Patent [19]
Augur

[11] Patent Number: 5,123,745
[45] Date of Patent: Jun. 23, 1992

[54] SYSTEM FOR VISUALLY DETERMINING THE HUE AND VALUE OF PAINT

[76] Inventor: Robert V. Augur, 7549 Cerrito Rojo Dr., Rancho Cucamonga, Calif. 91737

[21] Appl. No.: 673,346

[22] Filed: Mar. 22, 1991

[51] Int. Cl.⁵ .............................................. G01J 3/52
[52] U.S. Cl. ................................... 356/421; 40/310; 215/365; 434/98
[58] Field of Search ............... 356/402, 412, 421, 422, 356/423, 424, 425; 40/310; 215/365, 366; 434/84, 98-105

[56] References Cited

U.S. PATENT DOCUMENTS

| | | | |
|---|---|---|---|
| 241,655 | 5/1881 | Heeren | 356/423 |
| 517,367 | 3/1894 | Spence | 356/423 |
| 1,293,793 | 2/1919 | Kaddatz | 356/423 |
| 2,009,943 | 7/1935 | Munsell et al. | 356/421 |
| 2,209,764 | 7/1940 | Cassen et al. | 356/422 |
| 2,285,709 | 6/1942 | Gordon | 434/100 |
| 2,452,385 | 10/1948 | Merckel | 356/412 |
| 4,877,580 | 10/1989 | Aronowitz et al. | 356/422 |
| 4,904,604 | 2/1990 | O'Brien et al. | 356/424 |
| 5,009,507 | 4/1991 | Katz | 356/421 |

Primary Examiner—F. L. Evans
Attorney, Agent, or Firm—Harlan P. Huebner

[57] ABSTRACT

A system for visually determining the hue and value of a paint in transparent container by use of at least one label on said container having color bands that terminate in an edge of the label juxtaposed to the paint for direct side by side comparison.

10 Claims, 1 Drawing Sheet

SYSTEM FOR VISUALLY DETERMINING THE HUE AND VALUE OF PAINT

BACKGROUND OF THE INVENTION

1. Field of the Invention.

This invention relates to a system for visualizing hue and value of paint by a color wheel and gray scale applied to at least one label for affixation to a clear container of paint wherein the spectral color within the container may be read against the wheel and scale to establish color theory.

2. Description of Prior Art.

A color wheel for the recognition of various colors as well as assisting an artist as to that colors are complementary has been known and used since its basic development by Sir Isaac Newton in the mid-1660's. The most widely used system of colorimetry is that adopted in 1931 by the Commission Internationale de I' Eclairage or Commission on Illumination. The system was revised in 1964 and employs values to red, green and blue designating then the three primary colors from which all other colors are derived. To the primary colors have been added other colors on the wheel to a color wheel of today includes twelve colors.

The grey scale was developed to establish the value of the paint by lightness or darkness of a color and moves from black usually a "O" valve to white a "10" value with shades of grey inbetween.

In today's art world there are various physical color wheels that are usually cardboard wheels with the twelve colors spaced around the periphery. Usually somewhere on the cardboard is a grey scale. However, the color wheel and grey scale are not associated with any specific container of paint. A person could hold up the cardboard wheel next to the container to endeavor to establish the color in the container. This is cumbersome and requires a bending of the wheel to obtain any type of true reading.

In addition, where a grey scale is within the wheel and not marginally positioned it is extremely difficult, if not impossible, to obtain a true lightness or darkness value of the color in the container.

SUMMARY OF THE INVENTION

It is a purpose of the present invention to provide a label or labels on a transparent paint container wherein a color wheel and grey scale is placed thereon so that the colors and grey tones will extend to an edge adjoining the container and thus "bleed" into the paint color therein or are juxtaposed therewith.

Another object of the present invention is to provide a label or labels on a transparent paint container wherein the colors of the color wheel are peripherally arranged on the label forming the border of the label.

A further object of the present invention is to provide a grey scale wherein the scale from black to white with shades of grey therebetween terminates adjacent the painter container forming at least a portion within or on a border of the label.

A yet further object of the present invention is to provide a label or labels wherein a color wheel and grey scale is placed thereon with color letter abbreviations or numerical grey values are imprinted over the color.

Another object of the present invention is to provide a label or labels on a transparent paint container wherein a color wheel is placed thereon whereby the color therein may be compared with and next to same or complimentary colors to help establish color theory.

These and other objects and advantages will become apparent from the following part of the specification wherein details have been described for the competence of disclosure, without intending to limit the scope of the invention which is setforth in the appended claims.

BRIEF DESCRIPTION OF THE DRAWINGS

These advantages may be more clearly understood from the following detailed description and by reference to the drawings in which.

DETAILED DESCRIPTION OF THE PREFERRED EMBODIMENT

Figure 1:
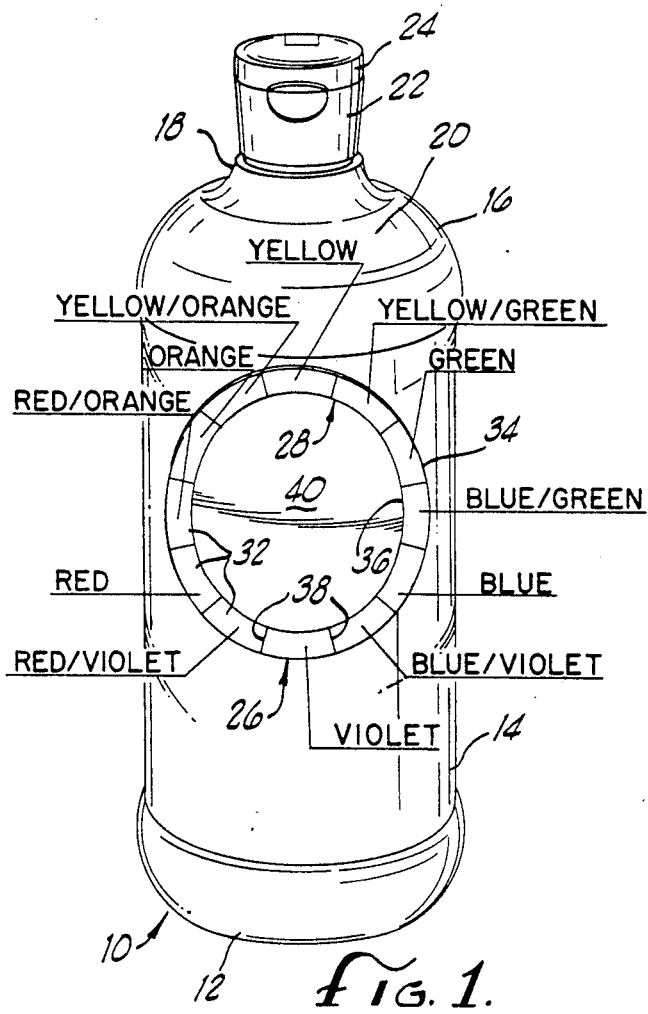
FIG. 1 is a side elevational view of the transparent paint container with the present invention of a color wheel label mounted thereon.

In FIG. 1 there is illustrated a bottle or container designated 10 that may be conventional in nature.

The bottle 10 is formed of a transparent material such as a clear flexible plastic. A clear bottle 10 is required for reasons to become apparent.

The bottle 10 has a bottom 12, annular side wall 14, a top portion 16 that tapers upwardly into a neck portion 18 through which the container 10 is filled with or emptied of paint 20.

The neck portion 18 usually includes a threaded exterior, not shown, to which is threadably secured a conventional closure cap 22. The cap 22 may have a hinged top 24 to dispense the paint 20.

In addition, while the container 10 is shown as annular, it could be made square or any other shape as long as it has a transparent side or sides. Because paint 20 is placed therein and to be able to obtain true colors and values therefrom a good degree of clarity and transparency of the material forming the container is desirable.

Positioned on the wall 14 of the container 10 is at least one label designated 26 containing bands of colors or a graphic color wheel designated 28 and/or bands or a grey scale designed 30. The label 26 may be made of paper and affixed to the container 10 by adhesive not shown.

The label 26, as seen in FIG. 1, is preferably round with the usual twelve colors of a color wheel circumferentially arranged around the margin of the label 26.

Each of the colors form an arcuate band 32 on the label with an outer edge 34 being the outer edge of the label 10 and an inner edge 36. Each band 32 has ends 38 which define the arcuate band and each band 32 abuts the next color.

In the case of the label 10 in FIG. 1 the actual color such as "yellow/green" is printed on the label 10. The different colors then proceed around the label margin and are arranged in the classic recognized fashion such as shown, "yellow, yellow/green, green, blue/green" etc.

Thus, as shown with the color bands 32 extending to edges 34 they will "bleed" into the color of the paint 20 in container 10, and are juxtaposed with the paint in the container. In this way the user can visually in side by side relationship compare the color 20 of the color band 32 with ease to determine the color and other characteristics. In addition, with the juxtaposition of the color bands to the paint 20, the user may compare or choose complimentary colors, that is a color diametrically across the circle or intermediate colors for proper color mix or information.

The center section 40 of the label 10, that is the area enclosed by the color bands 32 is to receive indicia. It may be the trademark, company name or other information such as ingredients, etc. Usually the area of the label to receive indicia is relatively large compared to the area of the band of colors.

Figure 3:
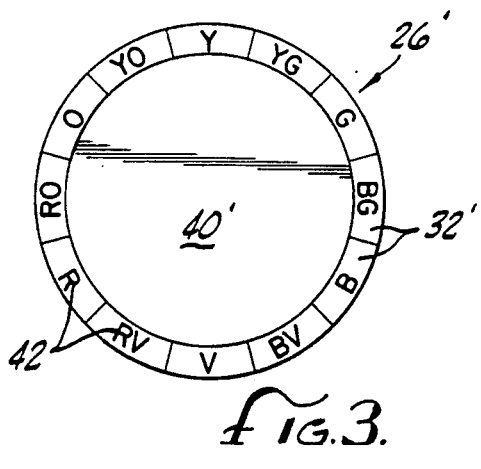
FIG. 3 is a modified color scale label where letters designating a particular color are positioned within the particular color.

Turning now to FIG. 3, this is a slight modification from the label of FIG. 1. Here label 26' is identical in shape and there are the same color bands 32'. However, the difference resides in the application of letters 42 over a portion of each band. The letters are to designate the particular color they are superimposed on, such as "YG" stands for "Yellow/Green", "RO" stands for "Red/Orange, etc.

Figure 2:
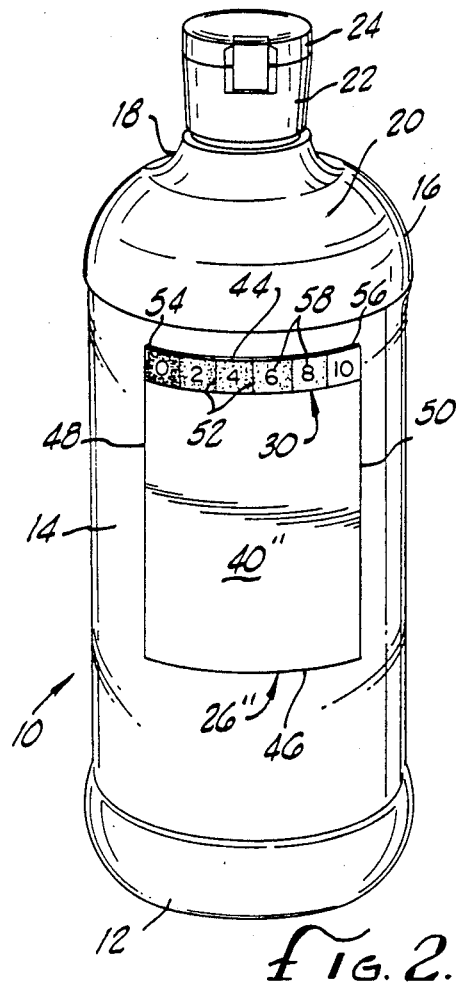
FIG. 2 is a side elevational view of a transparent paint container of FIG. 1 rotated 180 degrees with a second label containing a grey scale on a margin thereof to establish a paints value of lightness and darkness.

In FIG. 2 the grey scale 30 is illustrated on a label 26". Here the label is quadrilateral with parallel top and bottom edges 44 and 46 respectively and parallel side edges 48 and 50.

At the top of the label 26" is the scale 30 that extends across with grey bands 52 that extend from the edge 44 into the label. To some extend "gray scale" is a misnomer in that at one end of the grey spectrum is a black band 54 with a white band 56 at the opposite end.

In the illustration each band may be assigned a value number 58 which is used when comparing value which is the lightness or darkness of a paint color within the container 10.

With the various grey bands bleeding into the color of the paint 20 the process of determining the value is rendered much easier than previously possible.

The remaining portion 40" of the label 26" may be used for other indicia such as instructions, ingredients etc. However, it should also be recognized that the grey scale 30 may constitute the entire second label with no additional indicia thereon.

Figure 4:
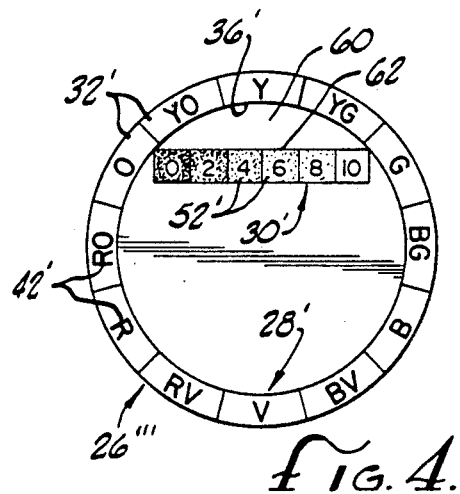
FIG. 4 is a further modified color scale label with a cutout therein bordered by a grey scale such as illustrated in FIG. 2.

In FIG. 4 there is illustrated another modified label 26''' with a graphic color wheel 28' and a grey scale 30' thereon.

The color wheel 28' is again made up of arcuate color bands 32' as defined before spaced around the label. The bands may just have the respective colors therearound or have letters 42' superimposed thereon.

The label 26''' has a window 60 cut out of it, preferable at the top. The window 60 is defined by the inner edge 36' of some of the bands 32' and a chord cut edge 62 across an arc of the label. With the label material removed to form the window 60 it can be seen that the paint 20 in the container 10 will show through and be juxtaposed with the scale 30'.

With the cut out the label 26''' may be printed with the grey scale 30' projecting across the chord with the edge 62 "bleeding" into the color showing through the window 60. The scale 30' is made up of the same grey shape bands 52' as previously discussed.

Again with the positioning of the gray scale 30' to the paint 20 the proper paint value may be easily determined.

The invention and its attendant advantages will be understood from the foregoing description and it will be apparent that various changes may be made in the form, construction and arrangements of the parts without departing from the spirit and scope thereof or sacrificing its material advantages, the arrangements herein before described being merely by way of example. I do not wish to be restricted to the specific forms shown or uses mentioned, except as defined in the accompanying claims, wherein various portions have been separated for clarity of reading and not for emphasis.

I claim:

1. A system for visually determining the hue or value of a paint that is in a transparent container comprising:
   at least one label affixed to said container adapted to fit the contour thereof and said label including bands of forms of differing colors one adjacent another and each having an outer edge forming an edge of at least a portion of said label whereby the edges are juxtaposed to said paint for direct side by side visual color or value comparison between said paint and bands of differing color; and
   said bands of color only include a relatively small area of the total area of said label.

2. A system as defined in claim 1 wherein there is:
   a first label for determining color, which is round and said bands of colors are color representations of twelve colors for colorimetry and said outer edge forms the edge of said label; and
   a second label affixed to said container for determining value mainly lightness and darkness of said paint wherein the bands vary from white to black with various shades of grey therebetween and said outer edge forms the edge of said label.

3. A system as defined in claim 2 wherein:
   said second label is a quadrilateral and said bands are arranged as a horizontal outer edge of said quadrilateral; and
   the area of said bands is relatively small as compared with the total area of said quadrilateral label.

4. A system as defined in claim 1 wherein:
   letters are superimposed on each band of differing color as an additional identification of the color within said band.

5. A system as defined in claim 2 wherein:
   numerals are placed in each band of said second label to afford a predetermined numerical value of each band.

6. A system as defined in claim 1 wherein:
   said label is round and said bands of colors extend around the perimeter of said label;
   a window cut out is provided within said label within the area not covered by said bands of colors; and
   bands including white and black with various shades of grey therebetween extended along a portion of said window and said outer edge forms the edges of a portion said window for side by side value comparison between said paint and said bands.

7. A system as defined in claim 6 wherein letters are superimposed on each band of differing color as an additional identification of the color within said band.

8. The combination of:
   a transparent container with an exterior surface and lid thereon;
   paint of a specific color within said container;
   at least one label affixed to said exterior surface of said container and adapted to fit the contour thereof, said label including bands of forms of differing colors one adjacent another and each having an outer edge forming an edge of at least a portion of said label whereby side by side color or value visualization of said paint color and said bands of color may be made; and said bands of colors only includes a portion of said label whereby the remaining portion may receive additional indicia thereon.

9. The combination of claim 8 wherein:

a second label is affixed to the exterior surface of said container containing bands that include a black band at one end, a white band at an opposite end and various shades of grey in between with each forming an outer edge of said second label whereby side by side visualization of said paint color and said bands may be made to visually determine the lightness and darkness value of said paint.

10. The combination of claim 8 wherein:

said label is round and said bands of differing colors extend around the perimeter of said label;

a window cut out provided in said label within the area not covered by said bands of colors; and bands including white and black with various shades of grey therebetween extending along a portion of said window and said outer edge forming the edge of a portion of said window for side by side value comparison between said paint and said bands.

* * * * *